United States Patent
Raju

[11] Patent Number: 6,149,584
[45] Date of Patent: Nov. 21, 2000

[54] IMA RETRACTOR

[76] Inventor: Seshadri Raju, 1020 River Oaks Dr., Suite 420, Jackson, Miss. 39208

[21] Appl. No.: 09/397,173

[22] Filed: Sep. 16, 1999

[51] Int. Cl.[7] ................................................. A61B 17/02
[52] U.S. Cl. .......................................... 600/232; 600/231
[58] Field of Search ..................... 600/228, 231, 600/232, 233

[56] References Cited

U.S. PATENT DOCUMENTS

| | | | |
|---|---|---|---|
| 1,400,616 | 12/1921 | McCrory et al. | 600/233 |
| 4,726,356 | 2/1988 | Santilli | 600/232 |
| 5,052,373 | 10/1991 | Michelson | 600/232 |
| 5,088,472 | 2/1992 | Fakhrai | 600/214 |
| 5,365,921 | 11/1994 | Bookwalter et al. | 600/232 |
| 5,772,583 | 6/1998 | Wright et al. | 600/232 |
| 5,846,193 | 12/1998 | Wright | 600/232 |
| 5,876,333 | 3/1999 | Bigliani | 600/231 |

*Primary Examiner*—Paul J. Hirsch
*Attorney, Agent, or Firm*—Roy, Kiesel & Tucker

[57] ABSTRACT

The invention is a sternal retractor comprising a curved crossbar and a pair of arms perpendicularly attached to the crossbar, at least one of which may slide over the length of the crossbar. Sternum engaging blades extend from the arms in a general direction from the concave side to the convex side of the retractor. The present invention lifts the ribcage, allowing access to the internal mammary artery while decreasing tissue damage associated with current retractors.

15 Claims, 1 Drawing Sheet

IMA RETRACTOR

BACKGROUND OF INVENTION

This invention relates to surgical retractors, particularly to sternal retractors used primarily in internal mammary artery (IMA) dissection.

To gain access to an internal mammary artery, a surgeon must split the patient's sternum and raise and retract one side of the rib cage. Many devices are known in the art which accomplish this. Typical designs comprise a toothed crossbar, a fixed arm attached to one end of the crossbar in a perpendicular orientation, and another arm, approximately parallel to the first, which may be moved along the crossbar with a crank mechanism to alter the spread of the arms. Each of the arms has a retractor blade attached near its end that is used to make contact with the sternum.

Many variations from this basic design exist in the art and are intended at least in part to help regulate the magnitude and direction of the force applied to sternum. If the spreading or lifting force is applied unevenly, nerve and tissue damage, as well as cracked ribs can result. A common variation is in the design of the retractor blades which vary in size, shape, and freedom of motion. The art also includes various designs for frames that connect the retractor mechanism to a fixed object such as an operating table to provide leverage and stability.

Many designs use a straight crossbar, which has one disadvantage. These retractors exert force in only one plane, that which is parallel to ground level during surgery, i.e. they provide a spreading force but no lifting force. To lift the sternum, a tilting force must be applied to the crossbar manually. This can cause excessive, uneven forces and undesirable stress concentrations at contact points.

Several alterations to the straight crossbar are known. One design (U.S. Pat. No. 5,088,472) utilizes a crossbar that is curved in the plane that is parallel to ground level during use. The arms are positioned on the concave side of the crossbar when the retractor is used below the chest, and positioned on the convex side when the retractor is used above the chest. This design gives the arms a non-parallel orientation and creates a variation in the spread width from one end of the retractor blades to the other. As a result, the more flexible lower ribs are spread at a rate greater than the upper ribs, lessening the chance for injury. However, the insufficient lifting force problem remains because the crossbar is curved only in a plane parallel to ground level.

Another design (U.S. Pat. No. 5,772,583) has its crossbar is bent downward so that it approximately conforms to the patient's body during use. This design is meant to reduce interference with the surgeon's field of movement, but it fails to provide a sufficient lifting force. In fact, this design creates a downward force that is less desirable than the force created by the average straight crossbar.

Designs that use a frame attached to a fixed object are more stable and generally direct the force more advantageously. However, they are inherently more complicated, and their bulk can interfere with the movement and vision of the surgical team.

ADVANTAGES AND OBJECTS OF THE INVENTION

It is an object of the present invention to provide a surgical retractor primarily for IMA procedures that is simple and easy to use, yet capable of simultaneously applying a lifting and spreading force.

It is also an object of the invention to minimize unnecessary forces on the rib cage to avoid the fractures and tissue damage which can result with the prior art.

Another object of the invention is to minimize interference with the vision and movement of the surgical team.

Still another object of the invention is to allow work on either side of the chest without additional difficulty.

SUMMARY OF INVENTION

The present invention is a retractor apparatus comprising a curved crossbar with a convex and a concave side, a first arm attached to the crossbar, a second arm movably attached to the crossbar, and a retractor blade mounted on each of the arms. The retractor blades extend from the arms in a general direction from the concave side of the crossbar to the convex side of the crossbar.

The present invention also includes a method for opening a sternum and lifting a ribcage for surgery using the apparatus described above. The process comprises cutting open the sternum, providing the retractor apparatus, placing the retractor blades between sternal halves, and operating the apparatus until the sternal halves have opened the proper distance.

DETAILED DESCRIPTION OF THE INVENTION

Figure 1:
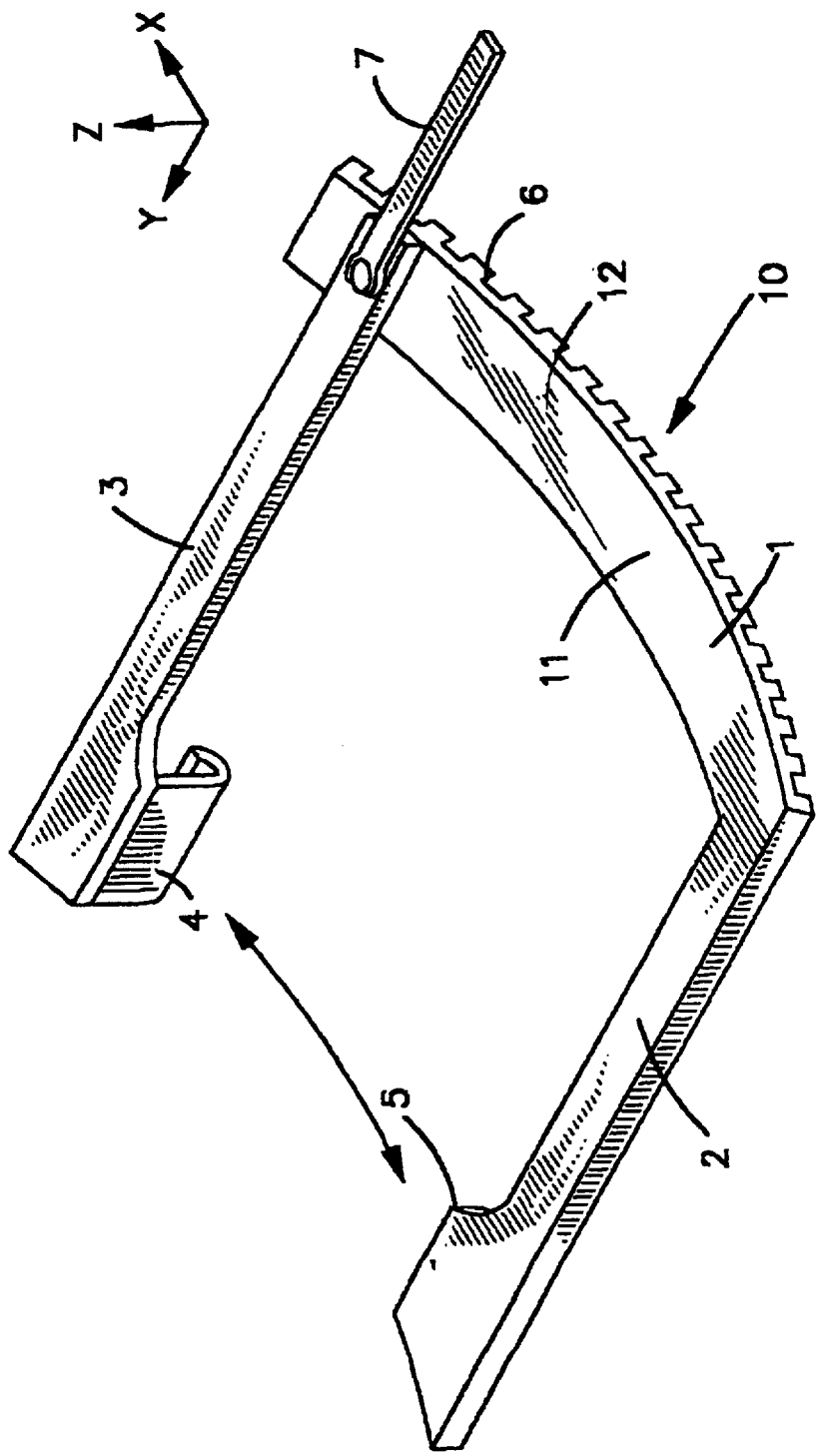
FIG. 1 illustrates a top view of an embodiment of the invention.

FIG. 1 illustrates a sternal retractor 10, for use in internal mammary artery surgery. Retractor 10 comprises crossbar 1, preferably having a rectangular cross section. At one end of crossbar 1, arm 2 attaches, preferably perpendicularly to crossbar 1. Arm 3 connects to crossbar 1, parallel to arm 2, so that arm 3 may move along the length of crossbar 1. Arms 2, 3 are preferably straight, but can be modified. For example, the addition of a slight bend may provide a better anatomical fit. Arms 2, 3 should be approximately 10 inches in length.

Crossbar 1 is curved about the y-axis. In one embodiment, the curvature forms a quarter circle, the circle having a radius of approximately 8 inches (the radius of curvature). The resulting curved crossbar has an arc length of approximately 12 inches. When retractor 10 is in use, concave side 11 should face in the z direction, away from the patient.

Figure 2:
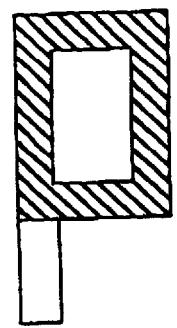
FIG. 2 illustrates a framed retractor blade.

Retractor blades 4, 5 are attached at the ends of arms 2, 3 opposite crossbar 1. They extend generally in a direction from concave side 11 of retractor 10 to convex side 12. When arms 2, 3 are positioned in the center of crossbar 1, blades 4, 5 extend downwardly along the z-axis. Blades 4, 5 are preferably detachable from arms 2, 3 and replaceable with blades of various lengths and shapes. They may also be made rotatable about each axis to allow them to better conform to the shape of a given patient's anatomy. Retractor blades 4, 5 may have a framed shape, i.e. a length of material surrounding an open space which increases visibility during a procedure. A framed blade is depicted in FIG. 2. Typical blade dimensions range from 1–3 inches in length (the direction parallel to the arms) and 1–2 inches in width. It is possible to obviate the need for separate blade structures by shaping arms 2, 3 so that they can engage the sternal halves.

One design which enables arm 3 to slide and lock includes teeth 6 along one side of crossbar 1. Teeth 6 are used in combination with a pinion mechanism (not shown) and crank 7 to provide the leverage and sensitivity necessary to achieve and maintain the proper spreading force.

An example of use of the device is as follows. If the left internal mammary artery is to be harvested using the device shown in FIG. 1, the sternum is cut and retractor blades 4, 5 are placed between the two halves of the sternum. Retractor 10 is positioned so that arms 2, 3 extend away from the sternum in a head-to-toe direction. Using this configuration crossbar 1 is on the feet side of the sternum. Convex side 12 faces the patient, and retractor blades 4, 5 extend toward the patient. Arm 3 is moved using crank 7 to its farthest left position so that it is adjacent to arm 2. Crank 7 is slowly turned until the proper separation and lift has been achieved for the left rib cage. Access to the artery is then available.

If access to the right artery is desired, retractor 10 is positioned so that crossbar 1 is on the head side of the sternum, and retractor blades 4, 5 are at the sternum. Convex side 12 faces the patient, and retractor blades 4, 5 extend toward the patient. Arm 3 is moved adjacent to arm 2. Blades 4, 5 are placed between the halves of the cut sternum so that blade 4 acts on the sternal half on the patient's right side. Crank 7 is then used to separate and lift the rib cage. Alternatively, retractor 10 could have the positions of arms 2 and 3 reversed.

What is claimed is:

1. A retractor apparatus comprising:

(a) a curved crossbar having a convex and a concave side, (b) a first arm attached to said curved crossbar; and (c) a second arm movably attached to said curved crossbar, said first and second arms adapted to mount a retractor blade on the end of said arms distal from said curved crossbar, such that when said retractor blades are mounted thereon, said retractor blades extend from said arms in a general direction from said concave side of said curved crossbar to said convex side of said curved crossbar.

2. The retractor apparatus of claim 1, further comprising retractor blades mounted to said arms.

3. The retractor apparatus of claim 1, further comprising teeth on at least one side of said curved crossbar and a means for moving said second arm on said curved crossbar.

4. The retractor apparatus of claim 1 wherein said curved crossbar has a radius of curvature of between about 7–9 inches.

5. The retractor apparatus of claim 3 wherein said curved crossbar has a radius of curvature of between about 7–9 inches.

6. The retractor apparatus of claim 2 wherein said retractor blades are rotatably adjustable.

7. A retractor apparatus comprising:

(a) a curved crossbar having a convex and a concave side, (b) a first arm attached to said crossbar, engageable with tissue to be retracted, such that the portion of said arm used to contact the tissue extends from said arm in a direction from said concave side of said crossbar to said convex side of said crossbar; and (c) a second arm movably attached to said crossbar, engageable with tissue to be retracted, such that the portion of said arm used to contact the tissue extends from said arm in a direction from said concave side of said crossbar to said convex side of said crossbar.

8. The retractor apparatus of claim 7, further comprising teeth on at least one side of said curved crossbar and a means for moving said second arm on said curved crossbar.

9. The retractor apparatus of claim 7 wherein said crossbar has a radius of curvature of between about 7–9 inches.

10. A method of opening a sternum and lifting a ribcage for surgery comprising:

(a) cutting open the sternum, (b) providing a retractor apparatus comprising:

(i) a curved crossbar having a convex and a concave side, (ii) a first arm attached to said curved crossbar; and (iii) a second arm movably attached to said curved crossbar, said first and second arms adapted to mount a retractor blade on the end of said arms distal from said curved crossbar, such that when said retractor blades are mounted thereon, said retractor blades extend from said arms in a general direction from said concave side of said curved crossbar to said convex side of said curved crossbar, (c) mounting said retractor blades on said arms, (d) placing said retractor blades between sternal halves; and (e) operating said retractor apparatus until said sternum has been opened to a desired distance.

11. The method of claim 10, wherein said retractor apparatus further comprises teeth on at least one side of said curved crossbar and a means for moving said second arm on said curved crossbar.

12. The method of claim 10 wherein said curved crossbar has a radius of curvature of between about 7–9 inches.

13. The method of claim 11 wherein said curved crossbar has a radius of curvature of about 7–9 inches.

14. The method of claim 10 wherein said retractor blades are rotatably adjustable.

15. The method of claim 11 wherein said retractor blades are rotatably adjustable.

* * * * *